(12) United States Patent
Kim

(10) Patent No.: US 11,298,213 B2
(45) Date of Patent: Apr. 12, 2022

(54) CERAMIC BODIES HAVING ANTIMICROBIAL PROPERTIES AND METHODS OF MAKING THE SAME

(71) Applicant: James R. Glidewell Dental Ceramics, Inc., Newport Beach, CA (US)

(72) Inventor: Jae Won Kim, Irvine, CA (US)

(73) Assignee: James R. Glidewell Dental Ceramics, Inc., Newport Beach, CA (US)

( * ) Notice: Subject to any disclaimer, the term of this patent is extended or adjusted under 35 U.S.C. 154(b) by 658 days.

(21) Appl. No.: 16/167,950

(22) Filed: Oct. 23, 2018

(65) Prior Publication Data

US 2019/0117343 A1 Apr. 25, 2019

Related U.S. Application Data

(60) Provisional application No. 62/575,578, filed on Oct. 23, 2017.

(51) Int. Cl.
| | | |
|---|---|---|
| *A61C 8/00* | (2006.01) | |
| *A61L 24/00* | (2006.01) | |

(Continued)

(52) U.S. Cl.
CPC .......... *A61C 8/0013* (2013.01); *A61C 8/0012* (2013.01); *A61C 8/0018* (2013.01); *A61C 13/083* (2013.01); *A61K 6/58* (2020.01); *A61K 6/802* (2020.01); *A61K 6/818* (2020.01); *A61K 6/824* (2020.01); *A61L 27/34* (2013.01); *A61L 27/427* (2013.01); *C04B 41/4535* (2013.01); *A61C 5/73* (2017.02); *A61C 8/005* (2013.01); *A61C 8/008* (2013.01); *A61C 13/0022* (2013.01); *A61K 6/50* (2020.01); *A61K 6/56* (2020.01); *A61L 2430/12* (2013.01); *C08G 77/58* (2013.01); *C09D 183/14* (2013.01)

(58) Field of Classification Search
CPC ...... A61C 8/0012; A61C 8/0013; A61K 6/80; B29L 2031/7536; C04B 35/48; C04B 35/486; C04B 2235/3256; C04B 2235/616; A61L 2430/12
USPC ........................................ 264/19; 501/89–92
See application file for complete search history.

(56) References Cited

U.S. PATENT DOCUMENTS 5,954,724 A * 9/1999 Davidson ................ A61L 31/08
  606/76
8,298,329 B2 10/2012 Knapp et al.
(Continued)

OTHER PUBLICATIONS

Aranha et al. Effect of Trace Metals on Growth of *Streptococcus mutans* in a Teflon Chemostat. Infection and Immunity vol. 35, No. 2. Feb. 1982 pp. 456-460 (Year: 1982).*

(Continued)

*Primary Examiner* — Cachet I Proctor
(74) *Attorney, Agent, or Firm* — Charles Fowler

(57) ABSTRACT

A method for making a ceramic body comprised of a ceramic material having an inhibitory effect on bacterial growth is provided. A dental prosthesis may be made of a ceramic material that comprises a molybdenum-containing component on a portion of the prosthesis that contacts the gingival surface of a patient. In one method, a porous zirconia ceramic structure is shaped in the form of a dental prosthesis, and then infiltrated with a molybdenum-containing composition, before sintering to densify the ceramic structure.

14 Claims, 3 Drawing Sheets

(51) Int. Cl.
  *A61L 27/34* (2006.01)
  *A61C 13/083* (2006.01)
  *A61L 27/42* (2006.01)
  *A61K 6/58* (2020.01)
  *A61K 6/818* (2020.01)
  *A61K 6/824* (2020.01)
  *A61K 6/802* (2020.01)
  *C04B 41/45* (2006.01)
  *C08G 77/58* (2006.01)
  *C09D 183/14* (2006.01)
  *A61C 5/73* (2017.01)
  *A61C 13/00* (2006.01)
  *A61K 6/50* (2020.01)
  *A61K 6/56* (2020.01)

(56) References Cited

U.S. PATENT DOCUMENTS

| | | | |
|---|---|---|---|
| 9,095,403 B2 | 8/2015 | Carden et al. | |
| 9,162,013 B2 | 10/2015 | Guggenbichler et al. | |
| 9,365,459 B2 | 6/2016 | Carden et al. | |
| 9,434,651 B2 | 9/2016 | Carden | |
| D769,449 S | 10/2016 | Leeson et al. | |
| 9,505,662 B2 | 11/2016 | Carden et al. | |
| 9,512,317 B2 | 12/2016 | Carden et al. | |
| 2007/0172434 A1* | 7/2007 | Jernberg | A61K 6/20 424/49 |
| 2008/0241788 A1* | 10/2008 | Bauer | C22C 1/0433 433/167 |
| 2010/0057199 A1* | 3/2010 | Guggenbichler | C01G 41/00 623/1.46 |
| 2012/0214134 A1 | 8/2012 | Khan et al. | |
| 2012/0315261 A1* | 12/2012 | Shin | A61K 36/02 424/94.2 |
| 2013/0316305 A1 | 11/2013 | Carden et al. | |
| 2016/0000538 A1 | 1/2016 | Park et al. | |
| 2016/0128932 A1* | 5/2016 | DuBourdieu | A61K 8/35 424/49 |
| 2017/0216000 A1* | 8/2017 | Jahns | A61C 13/277 |

OTHER PUBLICATIONS

Tetault et al. "Biocidal activity of metalloacid-coated surfaces against multidrug-resistant microorganisms". Antimicrobial Resistance and Infection Control. pp. 1-6. 2012 (Year: 2012).*

H. Aranha et al., Effect of Trace Metals on Growth of *Streptococcus mutans* in a Teflon Chemostat, Infection and Immunity, Feb. 1982, vol. 35, No. 2, pp. 456-460.

I. H. C. Gallagher et al., The Effect of Trace Elements on the Growth and Fermentation by Oral Streptococci and Actinomyces, Archs oral Biol., vol. 22, pp. 555-562, Pergamon Press 1977, Printed in Great Britain.

S. Guimond-Lischer et al., Silver ion doped TiN coatings with antibacterial and cytocompatible properties, eCM Meeting Abstracts 2017, Collection 3; SSB+RM, p. 43.

PCT application No. PCT/US18/57051, International Search Report and Written Opinion, dated Jan. 15, 2019, in 28 pages.

Kaplan et al., Production and properties of tooth-colored yttria stabilized zirconia ceramics for dental applications, Ceramics International 44 (2018) 2413-2418.

Patil et al., Synthesis, spectral and antibacterial studies of oxomolybdenum (V) and dioxomolybdenum (VI) complexes with 2-imidazolyl mercaptoaceto hydrazone, Scholars Research Library, Der Pharma Chemica, 2012, 4(5):1812-1818.

C. Zollfrank et al., Antimicrobial activity of transition metal acid MoO3 prevents microbial growth on material surfaces, Materials Science and Engineering C (2011), doi: 10.1016/j.msec 2011.09.010.

Tétault et al., Biocidal activity of metalloacid-coated surfaces against multidrug-resistant microorganisms, Antimicrobial Resistance & Infection Control 2012, 1:35, in 6 pages.

Mendel, Ralf R., Molybdenum:biological activity and metabolism, The Royal Society of Chemistry, Dalton Trans. 2005, 3404-3409.

International Preliminary Report on Patentability and Written Opinion in PCT International Application No. PCT/US2018/057051 dated May 7, 2020 (8 pages).

* cited by examiner

CERAMIC BODIES HAVING ANTIMICROBIAL PROPERTIES AND METHODS OF MAKING THE SAME

RELATED APPLICATIONS

This application claims the benefit of and priority to U.S. Provisional Patent Application No. 62/575,578, filed Oct. 23, 2017, which is hereby incorporated by reference in its entirety.

BACKGROUND

Use of inorganic substances that form hydrogen cations in the presence of an aqueous medium for antimicrobial activity is known. U.S. Patent Publication No. 2010/0057199 teaches making active substances by incorporating composite metal oxide substances containing molybdenum and/or tungsten with resin. When the active substances are contacted with water, the formation of hydrogen ions causes the pH to lower in the aqueous medium. The composite metal oxide/resin may be formed as a layer on the surface of a substrate to achieve an antimicrobial effect in an aqueous medium.

Zollfrank et al. tested antimicrobial activity on titanium rods coated with a nearly amorphous gel coating consisting of a mixture of molybdates containing $[Mo_3O_{10}]^{-2}$ ions and hydrated $MoO_3$. Coated titanium rods were annealed at about 300° C., transforming the gel layer into blue crystalline $MoO_3$, and an antimicrobial effect was detected. However, upon annealing at 500° C., a significant decrease in antimicrobial activity occurred, and upon annealing coated titanium rods at 700° C. antimicrobial activity was no longer detected. (C. Zollfrank, et al. Materials Science and Engineering C (2011), doi: 10.1016/j.msec. 2011.09.010.)

SUMMARY

Ceramic, glass-ceramic, glass and bodies materials are provided that exhibit antimicrobial activity against harmful bacteria. A method for infiltrating a porous body with a liquid molybdenum-containing composition is also provided. In another embodiment, a method for incorporating a ceramic material comprising a molybdenum-containing component as a filler or second phase in a ceramic, glass-ceramic or glass body, is also provided. In a further embodiment, ceramic material comprising a molybdenum-containing component may be incorporated as a coating or glaze, for example, when making a porcelain body. The resulting structures have long term antimicrobial effectiveness, and are suitable for use in medical procedures having a risk of infection, such as joint replacement.

In dental applications, ceramic, glass-ceramic and glass materials having antimicrobial properties may be useful in preventing or reducing growth of bacteria associated with the formation of biofilms believed to cause cavities and gingivitis. Dental applications for an antimicrobial material include, but are not limited to, restorations and prostheses having a surface that contacts a gingival surface of a patient upon installation in the patient's oral cavity. Prostheses which may benefit from such materials include those that are installed subgingivally such as, implants placed in or on a patient's jaw, or healing abutments, and prostheses having a portion that is installed subgingivally (e.g., beneath gingiva or within a gingival crevice), such as temporary or permanent abutments that attach to restorations such as, a replacement tooth, bridge, or denture. Dental materials having an inhibitory effect on bacterial growth may be suitable for restorations including crowns, in-lays, on-lays, or dentures that contact a patient's gingival tissue, for example, between the gingiva and an implant or preparation tooth, or which abut a preparation tooth on an intaglio surface. Other applications include adhesive cement materials, polymer or resin-based materials, or direct restorative materials in which an antimicrobial component, such as an antimicrobial ceramic, has been incorporated.

In one method, a porous body is infiltrated with a liquid molybdenum-containing composition by painting or spraying an entire surface of the porous body with the liquid composition, or dipping the porous body into the liquid composition to infiltrate porosity of the porous body. In other embodiments, the liquid molybdenum-containing composition may be selectively applied to an intaglio surface of a restoration that abuts an implant or preparation tooth (a patient's tooth that has been prepared or reduced for receiving the dental restoration crown), or at the crown margin that abuts a patient's gingival surface surrounding a preparation tooth or implant site when installed in the mouth of a user. Porous bodies having a network of interconnected pores may be fully infiltrated, or partially infiltrated, by the liquid antimicrobial composition. In other embodiments, where a portion of the porous network comprises closed pores, the porous body may be partially infiltrated by an antimicrobial composition. After infiltration of the antimicrobial composition into the porosity of the ceramic body, the ceramic body may be heated or sintered to partial or full density.

In one embodiment, a zirconia ceramic body comprising antimicrobial properties is made by a method comprising the steps of coating a porous zirconia ceramic body with an aqueous molybdenum-containing composition, wherein the aqueous composition comprises a molybdenum salt in an amount ranging from 0.015 wt % to 2 wt % molybdenum salt, based on the total weight of the aqueous composition; at least partially infiltrating the aqueous antimicrobial composition into the porous structure of the zirconia ceramic body; and then, sintering the infiltrated porous ceramic zirconia body, wherein the resulting sintered ceramic body inhibits bacterial growth in a region in which the molybdenum-containing composition was applied. The step of shaping the porous zirconia ceramic body into a dental restoration shape such as a dental implant or crown, may occur before or after the coating, infiltrating, or sintering step.

In one embodiment, a ceramic body is provided that advantageously comprises antimicrobial activity against bacteria even after sintering in oven temperatures greater than 800° C. The sintered ceramic body has an inhibitory effect against bacteria believed to be pathogenic, including *Streptococcus mutans* (*S. mutans*), associated with biofilm formation resulting in tooth decay, and *Porphyromonas gingivalis* (*P. gingivalis*) associated with chronic periodontitis, when tested by the methods described herein.

DETAILED DESCRIPTION

Figure 1:
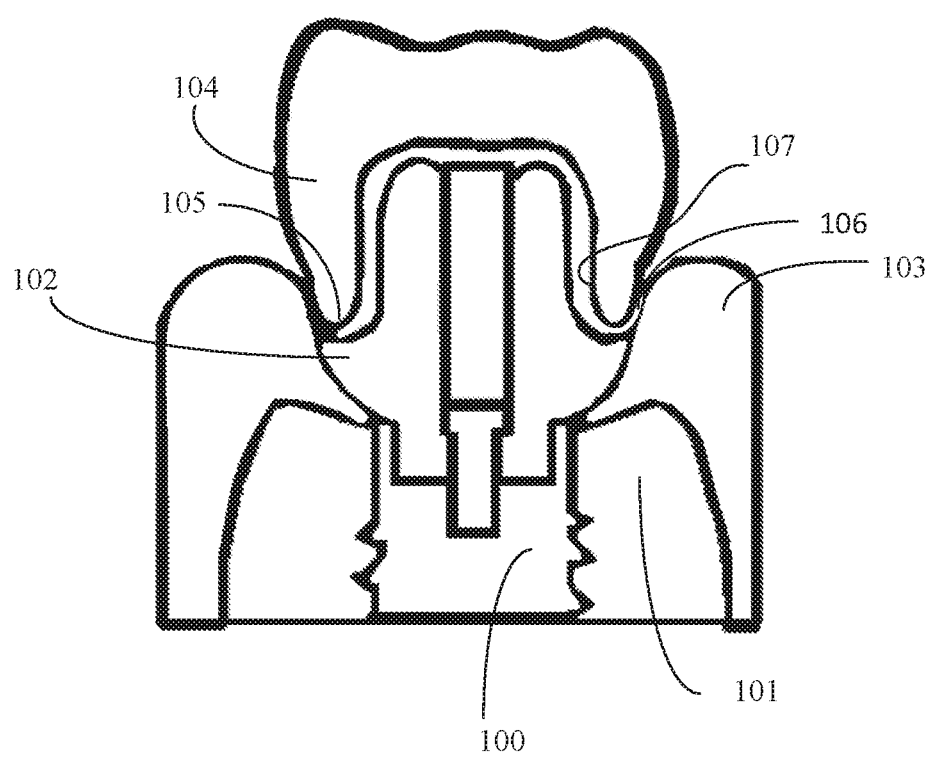
FIG. 1. An illustration of an example of an implant installed in a jaw on which an abutment and a dental restoration crown are connected.

Ceramic, glass-ceramic and glass materials having antimicrobial properties are provided. In one method, a porous body, such as a green stage or bisque stage ceramic body is infiltrated with a molybdenum-containing composition prior to or during a sintering process. In another embodiment, a ceramic, glass or glass-ceramic body comprises a filler or second phase material, such as a ceramic that comprises a molybdenum-containing component. In another embodiment, a ceramic crown restoration or a porcelain body comprises a coating or glaze that contains a molybdenum-containing component, or a filler material comprising a molybdenum-containing component.

A molybdenum-containing component is provided that comprises a source of molybdenum in the final body that imparts antimicrobial activity. The source of molybdenum may be organic, organo-metallic or inorganic. A molybdenum-containing component may be included in a polymer-molybdenum salt system and/or a molybdenum-containing resin system, including, but not limited to, dental/denture base resin systems, such as, polyurethane, acrylic systems, such as PMMA (polymethyl methacrylate), or PVA. Molybdenum-containing salts include, but are not limited to, molybdenum chloride (e.g., MoCl3 or MoCl4), including molybdenum (V) chloride (MoCl5), molybdenum-2-ethylhexanoate (Mo [OOCCH(C2H5)C4H9]4), ammonium heptamolybdate ((NH4)6Mo7O24.4H2O), cyclopentadienylmolybdenum(V) tetrachloride (C5H5C14Mo), and molybdenum(VI) oxide bis(2,4-pentanedionate) (C10H14MoO6).

A molybdenum-containing component may be dispersed, dissolved or hydrolyzed in a liquid such as water, organic solvent, inorganic solvent, or combinations thereof, to form a molybdenum-containing composition. A liquid molybdenum-containing composition may be a solution, suspension or a colloidal dispersion. Liquid molybdenum-containing compositions may comprise 0.015 wt % to 5 wt % molybdenum-containing salt based to the total weight of the liquid molybdenum-containing composition. In other embodiments, the concentration of molybdenum-containing salt is between 0.02 wt % and 3 wt %, or between 0.02 wt % and 2.5 wt %, or between 0.02 wt % and 2 wt %, or between 0.02 wt % and 1 wt %, or between 0.02 wt % and 0.5 wt %, or between 0.02 wt % and 0.2 wt %, or between 0.02 wt % and 0.1 wt %, or between 0.015 wt % and 0.5 wt %, or between 0.015 wt % and 0.1 wt %, or at least 0.015 wt % and less than 0.1 wt %, or at least 0.02 wt % and less than 0.1 wt %, based on the total weight of the liquid molybdenum-containing composition.

Molybdenum salts also may be mixed directly into liquid polymer or resin-based systems, including those described above, to form a molybdenum-containing composition, at a concentration of between 0.015 wt % and 5 wt %, or between 0.02 wt % and 3 wt %, or between 0.02 wt % and 2.5 wt %, or between 0.02 wt % and 2 wt %, or between 0.02 wt % and 0.5 wt %, or between 0.015 wt % and 2 wt %, between 0.015 wt % and 1 wt %, or at least 0.015 wt % and less than 0.1 wt %, of the molybdenum salt, based on the total weight of the polymer or resin based molybdenum-containing composition. Liquid polymer and resin-based systems include uncurable, or curable, including, but not limited to, light and/or heat curable systems known for use in dental applications comprising for example, epoxy, polyurethane, PMMA, or PVA, compositions.

Techniques for applying a molybdenum-containing composition to a porous body may include spraying, coating, painting (e.g., with a brush or pen), dripping or dipping, to infiltrate or penetrate the porous body with a liquid molybdenum-containing composition. A porous body may be fully immersed into a container containing the liquid molybdenum-containing composition for sufficient time to infiltrate the entire thickness of the ceramic body. In some embodiments, a molybdenum-containing composition may be applied to infiltrate a surface of a porous ceramic body configured to be non-visible when the finished dental prosthesis is installed in the mouth of a patient. For example, a molybdenum-containing portion may be configured to be located subgingivally, beneath the gums or gingival tissue, or an intaglio surface abutting an edentulous ridge or preparation tooth, or within a gingival crevice between gingival tissue and an implant or preparation tooth neck or root, when the finished dental prosthesis is installed in the mouth of a patient.

With reference to FIG. 1, a molybdenum-containing composition may infiltrate a surface of an implant (100) that is placed in the jaw (101) of a patient. A molybdenum-containing composition may be applied to infiltrate a portion of an implant abutment (102) or restoration that is configured to be placed subgingivally, beneath the gingival tissue (103) adjacent the implant (100) in a finished, sintered prosthesis. The molybdenum-containing composition may be selectively applied to only a subgingival portion of a restoration crown (104), for example, that is near a gingival margin (105) of the restoration in a gingival crevice (106), or to an intaglio surface (107) that abuts an implant, implant abutment or tooth preparation. Upon exposure to the molybdenum-containing composition, infiltration occurs through the entire thickness, or through only a portion of the thickness of the porous body. In other embodiments, a light spray or brush coating onto one or more surfaces of a porous body only partially penetrates the thickness of the porous body.

Figure 2A:
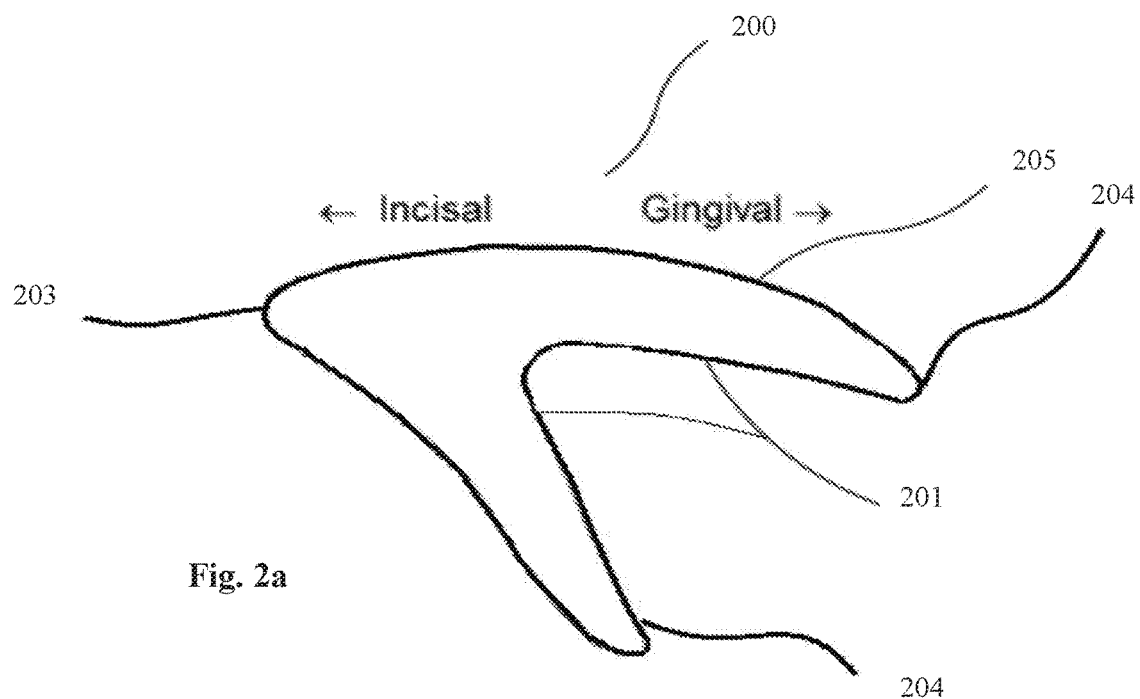
FIG. 2a and FIG. 2b. Cross-sectional illustrations of one embodiment of a dental restoration crown.
Figure 2B:
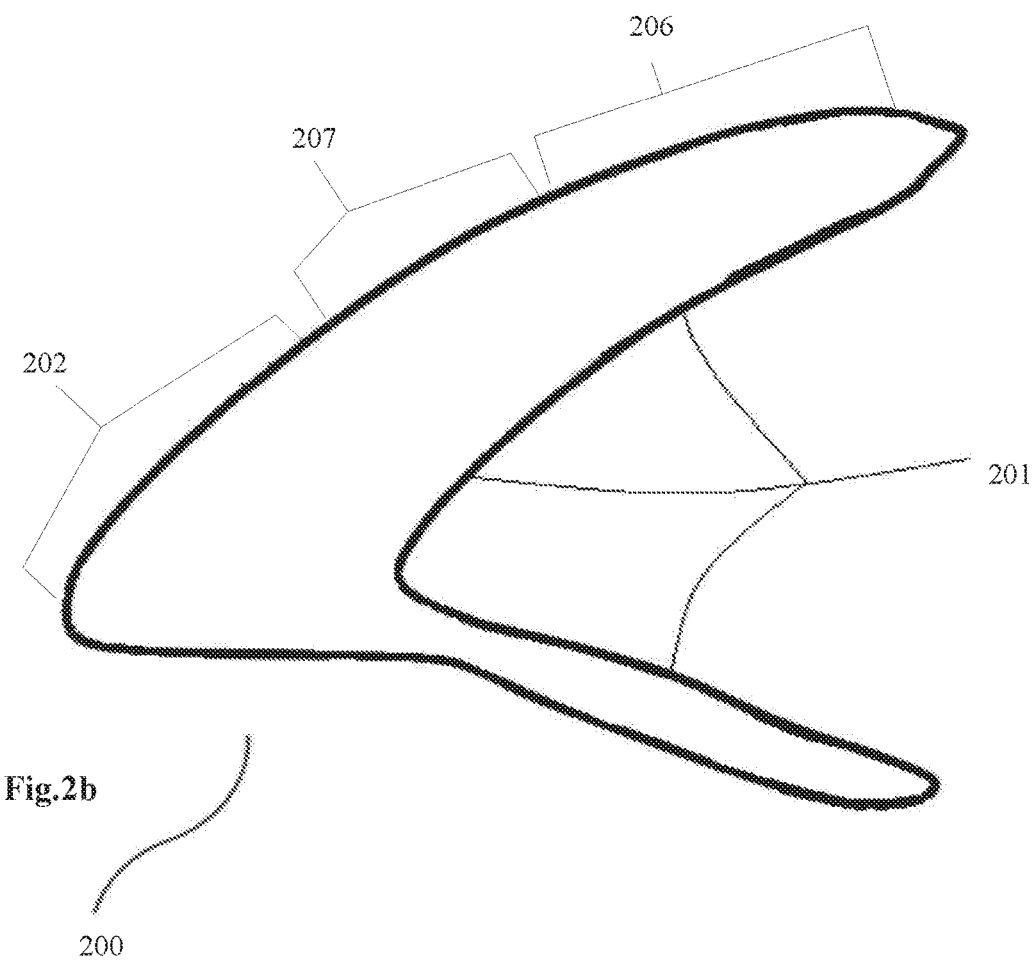

In an exemplary embodiment of the cross-sectional illustration of FIG. 2a and FIG. 2b, a molybdenum-containing composition may be applied to a dental restoration crown (200) on an intaglio surface (201) that abuts a preparation tooth (not shown) in a finished, sintered prosthesis. An antimicrobial composition may partially infiltrate the thickness of the porous body from an intaglio surface (201) without penetrating the vestibular (labial or buccal) surface (205) at an incisal region (202) or near the occlusal surface/incisal edge (biting surface) (203). An antimicrobial composition may be applied to the gingival margin (finish line) (204) of the porous body. In some embodiments, the composition may be infiltrated for a distance between 0 mm and 5 mm, or between 0 mm and 3 mm, or between 0 mm and 2 mm, or between 0 mm and 1 mm, or between 0 mm and 0.5 mm, from the gingival margin (finish line) (204), in the direction of the incisal edge (203). In one embodiment, a molybdenum-containing composition applied to a gingival margin (204) may be obscured below gingival tissues when the finished sintered prosthesis is installed.

In another embodiment, a molybdenum-containing composition may infiltrate a portion of the porous dental restoration crown (200) in a cervical region, for example, from the margin up to a cervical third (206), or less than or equal to half of the restoration closest to the finish line. The composition may optionally infiltrate a portion of the porous ceramic body between the margin and a middle third (207). The composition may be applied to the vestibular surface (205) of the cervical region, fully infiltrating the porous body from the intaglio surface (201) through to the vestibular surface (205), or only partially infiltrating the intaglio surface without wetting the vestibular surface (205). In some embodiments, an incisal/occlusal region (202) of the porous body, comprising, for example, an incisal third nearest the occlusal surface/incisal edge (203), and optionally, a middle third (207), has no molybdenum-containing composition, or less molybdenum-containing composition, than the cervical region. In some embodiments, only a portion of the dental restoration comprises enhanced antimicrobial activity in portions where the molybdenum containing composition is applied selectively. For example, antimicrobial properties may be greater at an intaglio (201) surface, or near a margin (204), or a cervical region (206), than on a vestibular surface (205) near the occlusal surface/incisal edge (203).

In another embodiment, a source of molybdenum is provided for infiltration into a ceramic by vapor infiltration. In one embodiment, an infiltration bed material is used in the vapor infiltration process that comprises a powder or particulate ceramic comprising a molybdenum-containing component. In one embodiment, the infiltration bed material is made by mixing a molybdenum-containing component into a ceramic slurry, and, if necessary, comminuting to form a ceramic powder or particulate material after drying. A ceramic structure is placed on, or submerged into, the infiltration bed material, and upon heating or sintering, molybdenum from the infiltration bed material vaporizes and diffuses onto and/or into the structure. In one embodiment, a molybdenum-containing component infiltrates into the pores of a porous ceramic body. In another embodiment, molybdenum coats, or infiltrates into, the structure of a densified, or non-porous, body in contact with the infiltration bed material through the vapor deposition technique.

In other embodiments, a ceramic filler or second phase ceramic material comprising a molybdenum-containing component may be used in a ceramic, glass-ceramic or glass body. In one embodiment, a ceramic slurry is mixed with a molybdenum-containing component or a molybdenum-containing composition, and then dried and, optionally, calcined to oxidize molybdenum, forming a ceramic filler having antimicrobial properties. The filler may be mixed, for example, with a ceramic powder, or components of a glass-ceramic or glass body, prior to shaping. In one embodiment, a ceramic body may comprise 0.001 mol % to 5 mol % molybdenum, or 0.01 mol % to 2 mol % molybdenum (calculated as metal ion), based on the total weight of the ceramic body.

In other embodiments, ceramic powder comprising a molybdenum-containing component may be used as a filler for a polymer matrix, a dental adhesive cement, and direct restorative materials, for dental restoration applications. In a further embodiment, a molybdenum-containing component or a molybdenum-containing composition may be combined with a porcelain material, such as a porcelain powder commercially available for use in dental applications comprised of, for example, silica and alumina, to form non-porous dental porcelain body having antimicrobial properties. A molybdenum-containing porcelain body may be formed by mixing porcelain powder and a liquid molybdenum-containing composition in a ratio of approximately 70 vol % to 90 vol % porcelain powder and approximately 10 vol % to 30 vol % a liquid molybdenum-containing composition described above, and then shaping the paste to form a porcelain body.

Optionally, the molybdenum-containing composition may further comprise additives. Pigments, such as organic pigments that burn off during a pre-sintering or sintering process, may be added to confirm application of the molybdenum-containing composition on the porous ceramic body. In another embodiment, a coloring agent may be added to the molybdenum-containing composition to form a mixture that imparts both antimicrobial properties and a desired shade upon sintering. A mixture of the molybdenum-containing composition and a coloring solution may be applied selectively to portions of the ceramic body, such as one or more of the incisal third, the middle third or cervical third of a dental restoration form, or the ceramic body may be dipped in the mixture for complete coverage. Alternatively, a molybdenum-containing component may be added with a coloring solution into a ceramic slurry, in accordance with the methods described in commonly owned U.S. Pat. Nos. 9,505,662, and 9,512,317, which are incorporated by reference, herein, in their entirety. The ceramic slurry mixture comprising a molybdenum-containing component and a colorant may be dried to form a ceramic powder or particulate infiltration bed material, or a filler component for a ceramic, glass, or glass-ceramic body.

In one embodiment, a molybdenum-containing coloring composition is formed that comprises a molybdenum-containing component and a metal-containing coloring agent. A molybdenum-containing component is added in a sufficient amount to provide antimicrobial properties in the final product. Metal-containing coloring agents suitable for use herein comprise metal compounds or metal complexes having one or more metallic elements of transition metals from groups 3-14 on the periodic table of elements, rare earth metals, or mixtures of transition metals and rare earth metals, that alter the shade of a final sintered body. A coloring agent may comprise a metal-containing component having metal(s) or metal ion(s) including but not limited to terbium, erbium, chromium, iron, cobalt, manganese, praseodymium, vanadium, titanium, nickel, copper, and zinc, and mixtures thereof, to provide a coloring effect. Metallic oxides, or metallic salts containing anions such as Cl—, $SO_4^{2-}$, $SO_3^{2-}$—, Br—, F—, $NO_2$—, and $NO_3$—, may be suitable for use as a coloring agent. The molybdenum-containing component and coloring agent may be formed, for example, as a solution, suspension or colloidal dispersion. In one embodiment, the molybdenum-containing component may be added to a coloring solution, such as those disclosed in commonly owned U.S. Pat. No. 9,095,403, which is incorporated by reference herein, in its entirety. Alternatively, the molybdenum-containing component and/or the coloring agent may be added as solids to an aqueous-based or solvent-based liquid, to form a solution, suspension or colloidal dispersion.

Porous bodies suitable for infiltration by the molybdenum-containing composition may include monolithic ceramic, glass-ceramic or glass bodies, and include, but are not limited to, ceramic green bodies, pre-sintered bodies or partially sintered bodies. Ceramic green bodies include those that have been dried or partially consolidated to a density below full theoretical density of the ceramic sintered form. Bisque stage ceramic bodies include those that have been densified, for example, by heating or pre-sintering to increase the density of the ceramic (e.g., to approximately 30% to 90%, or approximately 50% to 85%, of full theoretical density) while retaining residual porosity. The molybdenum-containing composition may fully or partially infiltrate a ceramic body that has interconnected porosity through its thickness, or the composition may partially infiltrate a ceramic body having discontinuous porosity, for example, at the surface.

In another embodiment, a fully sintered or fully dense body may be surface treated, for example, by sandblasting to roughen the surface; the molybdenum-containing composition may contact the surface and partially or fully infiltrate surface roughness or surface porosity formed by the surface treatment.

Ceramic bodies may comprise metal oxides such as alumina, zirconia, and yttrium, and mixtures thereof. Ceramic materials may further comprise a second phase or filler, such as an oxide of titanium, cordierite and/or mullite. Zirconia-alumina composite ceramic material may comprise a ratio of alumina to zirconia in a range of about 20 wt % alumina:80 wt % zirconia to 80 wt % alumina:20 wt % zirconia.

Zirconia ceramic bodies may comprise an amount of zirconia that is between 80 wt % and 100 wt % zirconia ceramic material, based on the total weight of the ceramic material before treatment with the antimicrobial component. In some embodiments, the amount of zirconia ceramic materials may comprise 85 wt % to 100 wt %, 85 wt % to 99.8 wt % or 90 wt % to 99.7 wt %, based on the weight of the ceramic body, and, optionally, minor amounts of other materials, such as alumina. Zirconia ceramic material includes unstabilized and stabilized zirconia (including fully and partially stabilized zirconia), and mixtures thereof. Stabilized zirconia may include yttria-stabilized tetragonal zirconia, ceria stabilized tetragonal zirconia (Ce-TZP), calcia partially stabilized zirconia (Ca-PSZ), magnesia partially stabilized zirconia (Mg-PSZ), and mixtures thereof.

Zirconia ceramic material suitable for use herein includes, but is not limited to yttria-stabilized zirconia commercially available from Tosoh USA, yttria-stabilized or partially-stabilized zirconia that has been stabilized with approximately 0.1 mol % to approximately 8 mol % yttria, or approximately 2 mol % to approximately 6 mol % yttria, or approximately 2 mol % to approximately 4 mol % yttria.

Ceramic powder may have substantially uniform particle size distribution, or may have an average particle size in a range from approximately 0.005 micron (µm) to approximately or approximately 0.05 µm to approximately 1 µm. Examples of ceramic material suitable for use herein also include zirconia described in commonly owned U.S. Pat. No. 8,298,329, which is hereby incorporated by reference in its entirety.

Ceramic bodies may be shaded or unshaded prior to incorporation of the molybdenum-containing composition, and may be formed from pre-shaded or unshaded ceramic material. Pre-shaded ceramic materials include commercially available millable, ceramic blocks that match a specific target shade or a shade range, for example, BruxZir® ceramic blocks (e.g., BruxZir® Shaded 16 series Glidewell Laboratories, Irvine, Calif.) in target shades matching VITA® Classic shades, or bleached shades.

A porous or pre-sintered ceramic body may be shaped as a block, disk, near net shape, or a preform that approximates the size and/or shape of a final body. Ceramic bodies, for example, may be made by known processes for pressing, slip casting, and automated processes, including additive (e.g., 3-D printing) and subtractive (e.g., milling) automated processes. Ceramic bodies may be made by processes described in commonly owned U.S. Pat. Nos. 9,365,459, 9,434,651, and 9,512,317, all of which are hereby incorporated in their entirety, herein. Pre-sintering methods may be conducted in accordance with directions provided by the manufacturer, or, for example in some embodiments, by heating at an oven temperature in the range of 900° C. to 1200° C. for 1 to 2 hours.

A porous bisque stage ceramic body may be infiltrated with the molybdenum-containing composition before or after shaping into a specific form. A ceramic body may be shaped in the form of a prosthesis, for example, as an implant, implant-abutment, on-lay, or a ceramic restoration, such a zirconia CAD/CAM denture or multi-unit bridge, or single unit crown, based on the individual requirements of a patient. Milling or automated processes for shaping the ceramic body into a dental restoration form may be performed prior to application of the molybdenum-containing composition, or after the application of the molybdenum-containing composition but before sintering, or after both application and sintering steps. An infiltrated ceramic material that is sintered prior to milling may comprise a ceramic preform or near net shape. Examples may be found in commonly owned U.S. Patent Publication No. 2013/0316305, and U.S. Pat. No. D769, 449, both of which are hereby incorporated herein by reference in their entirety.

Infiltrated ceramic bodies may be sintered to partial density, for example, between 50% and 99% of full, theoretical density. Infiltrated ceramic bodies may be sintered to at least 98% of full theoretical density in accordance with sintering instructions of the manufacturer of commercially available ceramic materials, or, for example, by heating the ceramic body in an oven heated at an oven temperature, for example, between about 1000° C. and 1600° C., for about 2 hours to 48 hours.

In one embodiment, a fully or partially densified ceramic body comprises a ceramic material that comprises an amount of molybdenum in the range of 0.01 ppm to about 600 ppm (when calculated as the metal ion). In other embodiments, the amount of molybdenum in the infiltrated portion is from 0.01 ppm to 500 ppm, or 0.01 ppm to 200 ppm, or 0.01 to 100 ppm, or 0.2 ppm to 40 ppm, or 0.3 ppm to 20 ppm, or 0.4 ppm or 10 ppm, or 0.4 ppm to 9 ppm, molybdenum (when calculated as a metal ion). A fully or partially densified ceramic body may comprise 0.001 mol % to 5 mol % molybdenum, or 0.001 mol % to 1 mol % molybdenum, or 0.002 mol % to 1 mol % molybdenum, or 0.002 mol % to 0.1 mol % molybdenum, or 0.002 mol % to 0.05 mol % molybdenum, or 0.002 mol % to 0.01 mol % molybdenum, or 0.0025 mol % to 0.05 mol %, or 0.0025 mol % to 0.035 mol %, or 0.0025 mol % to 0.015 mol %, molybdenum, when calculated as a metal ion, in the infiltrated portion.

Alternatively, the infiltrated portion of a sintered ceramic body may comprise 0.003 mol % to 0.2 mol %, or 0.003 mol % to 0.1 mol %, or 0.003 mol % to 0.08 mol %, or 0.003 mol % to 0.01 mol %, or 0.004 mol % to 0.1 mol %, or 0.004 mol % to 0.085 mol %, or 0.004 mol % to 0.08 mol %, or 0.004 mol % to 0.015 mol %, molybdenum, when calculated as the metal ion.

One exemplary method of making a sintered ceramic dental prosthesis for restoring dentition of a patient that inhibits bacterial growth, comprises: a) obtaining a porous ceramic body comprising a shape of a dental prosthesis; b) obtaining a liquid molybdenum-containing composition comprising from 0.015 wt % to 5 wt % of a molybdenum-containing component, based on the weight of the molybdenum-containing composition; c) infiltrating the liquid molybdenum-containing composition into a first portion of the porous ceramic body that corresponds to a portion of the sintered ceramic body that contacts a gingival surface of the patient; and c) sintering the infiltrated porous zirconia ceramic to form the sintered ceramic dental prosthesis. In some embodiments, an aqueous molybdenum-containing composition comprises 0.015 wt % to less than 0.1 wt % of molybdenum (V) chloride (MoCl$_5$) based on the weight of the molybdenum-containing composition. Where dental prosthesis is, optionally, an implant, the porous zirconia ceramic body may be fully infiltrated, or as a crown, the first portion corresponds to an intaglio surface or a margin, or as an implant abutment, the first portion corresponds to a subgingival portion. In a further embodiment, the porous body comprises a second portion that is not infiltrated with the aqueous molybdenum-containing composition, and the second portion corresponds to a vestibular surface of an incisal region of the sintered dental restoration.

Resulting sintered ceramic bodies have enhanced antimicrobial activity against pathogenic bacteria typically found in the human oral cavity. There may be a reduction in bacterial growth when sintered ceramic bodies comprising the molybdenum-containing component are tested according to methods described herein; lower bacterial growth is observed compared to similarly prepared sintered ceramic bodies without the molybdenum-containing component. Thus, ceramic materials prepared by the methods described herein exhibit an inhibitory effect. In one embodiment, a treated sintered ceramic body exhibits an inhibitory effect on the growth of S. mutans, P. gingivalis, or both.

In one embodiment, a resulting ceramic body for use in making a sintered ceramic dental prosthesis for a patient, may comprise a porous zirconia ceramic body in the shape of a dental prosthesis having a first portion corresponding to a portion of the sintered ceramic dental restoration configured to contact a gingival surface of the patient. A first portion may be comprised of a first zirconia ceramic material comprising 0.001 mol % to 2 mol %, or 0.002 mol % to 0.01 mol %, of molybdenum calculated as a metal ion. In some embodiments, the ceramic body comprises a second zirconia ceramic material having less molybdenum than the first portion, and the inhibitory effect of the first zirconia ceramic is greater than the inhibitory effect of the second zirconia ceramic material against the growth of S. mutans. In some embodiments, the first zirconia ceramic material exhibits an inhibitory effect on the growth of S. mutans, and a reduction of at least 98% after 2 months is observed.

The effectiveness in reducing bacterial growth compared to a control may be reported as a percent reduction in bacterial growth when tested according to the methods provided herein. In one embodiment, a sintered yttria-stabilized zirconia ceramic body exhibits an inhibitory effect on the growth of S. mutans, such as, S. mutans (ATCC #25175), providing a reduction of at least 50%, or at least 75%, when tested, for example, according to the Antimicrobial Activity test method of ASTM E3-2180-07 (2012). In some embodiments, the reduction in the growth of S. mutans is at least 89% or at least 95%, or at least 98%, or at least 99%, for more than 5 months, or more than 6 months, or more than 7 months, or more than 8 months, or at least 9 months, for example, compared to a control sample when tested according to the Antimicrobial Activity test method of ASTM E3-2180-07 (2012).

In another embodiment, a sintered ceramic body made according to the methods described herein exhibits an inhibitory effect on the growth of P. gingivalis, such as, a reduction of at least 80%, or at least 85%, or at least 90%, for P. gingivalis, compared to the control sample, when tested according to the method provided herein.

By infiltration into the porous body of a structure prior to sintering, the molybdenum component is durable against wear and solubility, and antimicrobial properties are long lasting. The resulting sintered ceramic bodies retain effectiveness against microbes without a substantial reduction in the amount inhibitory effect due to, for example, wearing away of the antimicrobial component over time. Sintered, ceramic bodies having antimicrobial effectiveness maintain acceptable flexural (3-point bend) strength and biaxial strength values that are suitable for use in anterior and/or posterior dental applications.

Test Methods

Determining the Activity of Incorporated Antimicrobial Agent(s) (ASTM E2180-07 (2012)).

The antimicrobial effectiveness of treated, sintered ceramic samples was measured for S. mutans (ATCC #25175). Flat, porous ceramic bodies were treated with an antimicrobial liquid prior to sintering. Sintered samples were prepared, and tested following ASTM E2180-07 test method.

After three subcultures, a 24 h bacterial culture was grown on growth media. Bacterial broth cultures were adjusted to 1–5×108 cells/mL with a spectrophotometer or cell counting chamber.

Agar slurry was prepared by dissolving 0.85 g NaCl and 0.3 g agar-agar in 100 mL of deionized water, sterilizing the dissolved agar in an autoclave for 15 min. at 121° C., 15 psi., and then cooling the agar to 45° C. (+/−2° C.). About 1.0 ml of the adjusted culture (1–5×108 cells/mL) was placed into the 100 mL agar slurry. The final concentration was about 1–5×106 cells/mL in the agar slurry. Serial dilutions of the agar slurry were made immediately from '0 hour' (0 h) control samples and each dilution was spread plated to determine CFU/mL recoverable at time 0 h.

Each ceramic body test sample was placed into a sterile 15×100 mm petri dish. A cotton swab was dipped into sterile 0.85% saline to pre-wet the test sample. 1.0 mL of inoculated agar slurry was pipetted onto the test samples and control samples as a thin layer; the samples were prepared in triplicate. The agar slurry inoculum was allowed to gel and then, the samples were placed in an incubator at 37° C. (+/−2° C.). The contact time of the inoculated slurry on the ceramic bodies was 24 hours (+2 hours).

Following the specified contact time, the incubation period control samples and incubation period treated samples were aseptically removed from the petri dishes to 120 ml containers containing a sufficient volume of Dey Engley (DE) neutralizing broth to form an initial 1:10 dilution of the original inoculum. Serial dilutions of the neutralizing broth were made; the growth media was tryptic soy broth.

Samples were vigorously mixed with a vortex mixer for 1 min. After mixing, the sample test surface was imprint-cultured onto tryptic soy agar in order to determine release efficiency of the inoculum from the treated surface. Serial dilutions were made from recovered slurry, spread plated and incubated at 37° C. for 48 hrs. Colony numbers were counted and recorded for each dilution plate. The percent reduction of bacterial growth was calculated as follows.

The geometric means of the number of organisms recovered from the triplicate incubation period, the control and incubation period treated samples were calculated by the following equation:

$$\text{Geometric mean} = \frac{\text{Log } X1 + \text{Log } X2 + \text{Log } X3}{3}$$

Where Log is Log10, and X is the number of organisms recovered from the incubation period control or incubation period treated samples.

$$\text{Percent reduction (\% reduction)} = \frac{a-b}{a} * 100$$

a=the antilog of the geometric mean of organisms recovered from the incubation period control samples;
b=the antilog of the geometric mean of the number of organisms recovered from the incubation.

Flexural Strength Test—3-Point Bend Strength

Flexure tests were performed on sintered test materials using the Instron—Flexural Strength following ISO 6872 for preparation of strength testing for dental ceramic; flexural strength bars were milled and prepared. Once prepared, the bars were placed centrally on the bearers of the test machine so the load applied to a 4 mm wide face was along a line perpendicular to the long axis of the test piece. Then force is applied and the load needed for breaking the test piece (loading rate was 0.5 mm/min) was recorded. The flexural strength is calculated using sample's dimensional parameter and critical load information.

Flexural strength, σ, in MPa was calculated according to the following formula:

$$\sigma = \frac{3PL}{2Wb^2}$$

where P is the breaking load, in newton; L is the test span (center-to-center distance between support rollers) in millimeters; W is the width of the specimen, i.e. the dimension of the side at right angles to the direction of the applied load, in millimeters; b is the thickness of the specimen, i.e. the dimension of the side parallel to the direction of the applied load, in millimeters. The mean and standard deviation of the strength data was reported. Means should equal or exceed the requirements.

Test bars were prepared by cutting bisque materials taking into consideration the targeted dimensions of the sintered test bars and the enlargement factor (E.F.) of the material, as follows:
starting thickness=3 mm×E.F.;
starting width=4 mm×E.F.; and
starting length=55 mm×E.F.

The cut, bisque bars were sintered and flexural strength was measured and calculated according to the 3-point flexural strength test described in ISO (International Standard) 6872 Dentistry—Ceramic Materials.

Biaxial Strength Test (Piston-on-Three-Ball Test)

Biaxial strength test was conducted according to ISO 6872. Universal mechanical testing machine, capable of a crosshead speed of (1±0.5) mm/min and an ability to measure applied loads of between 10 N and 5000 N (±1%) was used.

The Biaxial flexural strength test fixture had a sample test support of three hardened steel balls with a diameter (4.5±2 mm) positioned 120° apart on a support circle with a diameter (11±1 mm). The sample was placed concentrically on these supports and the load was applied with a flat punch with a diameter of (1.4±0.2 mm) at the center of the sample specimen.

Density

The density strongly depends on the composition and structure of the samples of the ceramic materials. Density calculations for ceramic bodies may be determined by liquid displacement method of Archimedes principle. Distilled water was used as the liquid medium. Densities of ceramic samples were calculated using the following formula:

$$\rho = \frac{(W^2 - W^1)}{(W^4 - W^1) - (W^3 - W^2)}$$

ρ=density (gram/cc);
W1=weight of empty specific gravity bottle (gram);
W2=weight of specific gravity bottle with sample (gram);
W3=weight of specific gravity bottle with sample and distill water (gram);
W4=weight of specific gravity bottle with distill water (gram).

A theoretical density of 6.08 g/mL was assumed for purposes of calculating relative density.

EXAMPLES

Example 1

Zirconia ceramic bodies infiltrated with a molybdenum salt solution were tested for antimicrobial properties over an incubation period of approximately 9 months.

Porous, white bisque stage BRUXZIR® HT 2.0 zirconia wafers (28 mm×28 mm×1 mm) were prepared by sanding the surface with #220 SiC sand paper. An aqueous solution was prepared consisting of molybdenum salt and water. The sanded surfaces were coated with 0.025 wt % molybdenum (V) chloride ($MoCl_5$) aqueous mixture and sintered for 25 hours at 1530° C. The sintered samples were inoculated and incubated according to the test method provided herein for Antimicrobial Activity (ASTM E2180-07 (2012)).

Figure 3:
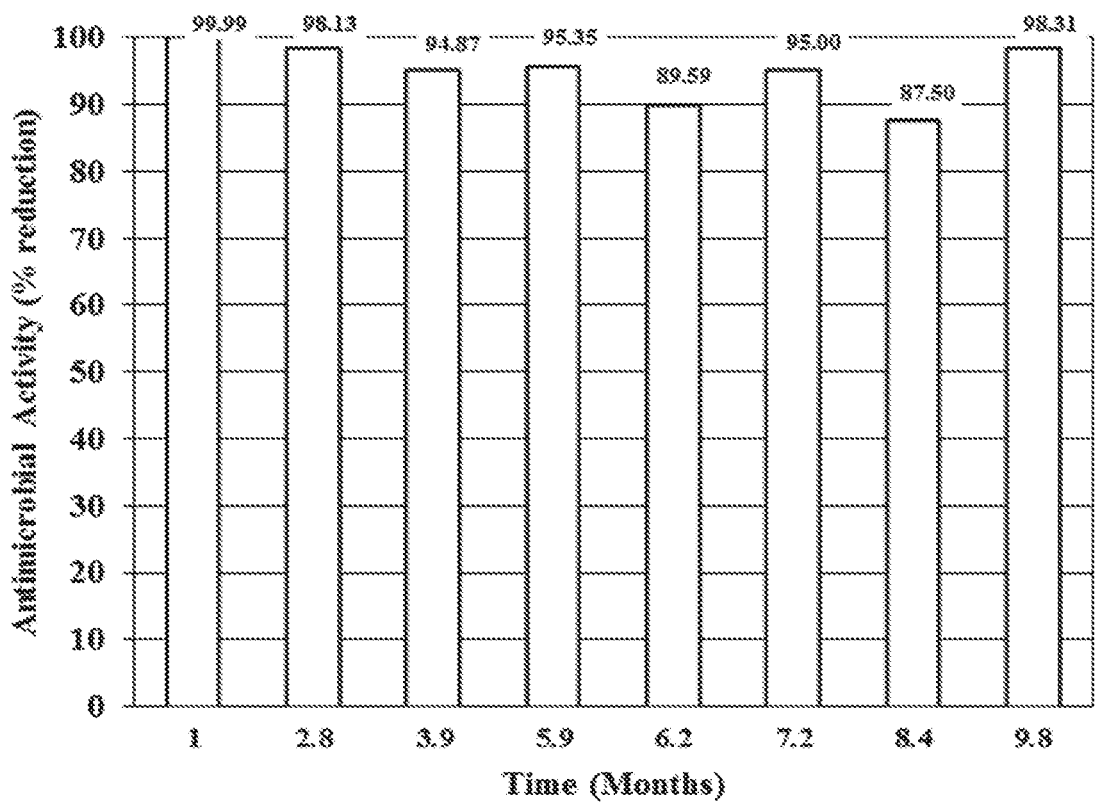
FIG. 3. Graph of percent reduction of *S. mutans* over time exposed to samples of treated sintered zirconia bodies.

The effectiveness of the sintered zirconia ceramic samples in reducing growth of *S. mutans* (ATCC® 25175™) was measured by calculating the percent reduction in bacterial growth (for three samples X1, X2, and X3) compared to a control sample. Results showing the percent reduction in bacterial growth for test samples comprising ceramic bodies treated with an aqueous mixture of 0.025 wt % $MoCl_5$ at 1.0 month (99.99% reduction), 2.8 months (98.13% reduction), 3.9 months (94.87% reduction), 5.9 months (95.35% reduction), 6.2 months (89.59% reduction), 7.2 months (95.0% reduction), 8.4 months (87.5% reduction) and 9.8 months (98.31% reduction), are illustrated in FIG. 3. The percent reduction in the growth of *S. mutans* is greater than 89% after 6 months, and the sintered ceramic bodies reduce the growth of *S. mutans* at least 87% after 9 months, when tested according to the Antimicrobial Activity test method of ASTM E3-2180-07 (2012).

Examples 2-3

Treated and untreated sintered zirconia ceramic bodies were tested for the effectiveness against the growth of *P. gingivalis*.

Porous, white bisque stage BRUXZIR® HT 2.0 zirconia bodies (10 mm×10 mm×1.6 mm) were prepared by sanding the surface with #220 SiC sand paper. Aqueous mixtures were prepared consisting of molybdenum salt and water. To form treated samples, 7 ceramic discs were immersed in a 0.025 wt % molybdenum (V) chloride ($MoCl_5$) aqueous mixture (Ex.2), 7 ceramic discs were immersed in 0.5 wt % molybdenum (V) chloride aqueous mixture (Ex. 3) and 7 control samples were not dipped in a solution. Treated and untreated bisque ceramic bodies were fully densified by sintering at 1530° C. for 2.5 hours.

To test the antimicrobial effectiveness, samples from each group and controls were immersed in 20 ml semi-defined biofilm medium of trypticase soy broth-based medium supplemented with hemin, vitamin K and cysteine which was inoculated with 5×107 CFU of P. gingivalis (ATCC #33277) culture maintained in a meat broth. Test samples and control samples were grown at 37° C. in an incubator in anaerobic conditions for 48 hours. Two samples were examined to confirm biofilm formation using a confocal microscope and scanning electron microscope. Five samples were prepared by rinsing in phosphate saline (pH 7) and removing biofilms by sonication. Serial dilutions were made (10-3, 10-4 and 10-5) and plated in triplicate on Columbia agar with hemin, vitamin K and cysteine. The bacterium was grown anaerobically for all conditions. The antimicrobial effectiveness of the samples against the growth of *P. gingivalis* was measured.

Figure 4:
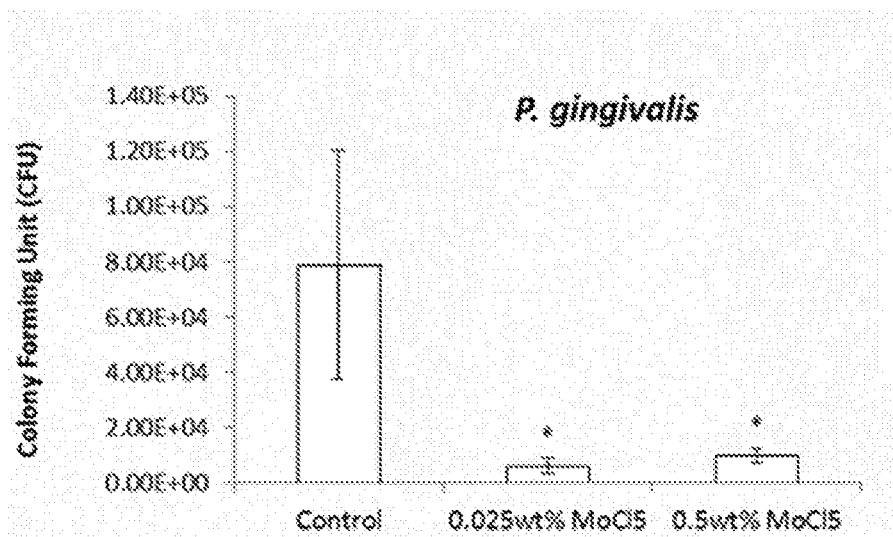
FIG. 4. Graph of colony forming units of *P. gingivalis* on treated and untreated zirconia bodies according to one embodiment.

The number of colony forming units (CFU) of bacteria grown on zirconia ceramic bodies, without a molybdenum-containing component and with two different concentrations of a molybdenum-containing component, are shown in FIG. 4. The results indicate that ceramic samples of Ex. 2 (0.025 wt % MoCl5) had an inhibitory effect, providing a reduction of 92% on the growth of *P. gingivalis*, and ceramic samples of Ex. 3 (0.5 wt % MoCl5) had a reduction of 88%, against *P. gingivalis*, compared to the control sample.

Ceramic bodies treated with either 0.025 wt % MoCl5 or 0.5 wt % MoCl5 exhibited significant inhibitory effectiveness against *P. gingivalis*.

Confocal micrographs of *P. gingivalis* demonstrate a higher level of dead bacteria for samples treated with 0.025 wt % MoCl5, than 0.5 wt % MoCl5 or the control Samples treated with 0.5 wt % MoCl5 demonstrated a higher level of dead bacterial cells than the control (C).

Examples 4-5

Bisque stage zirconia bodies were treated with an antimicrobial composition, sintered and tested for mechanical strength properties.

The effect of the antimicrobial compositions on the mechanical strength of sintered bodies was tested. Bisque stage 3 mol % yttria-stabilized zirconia ceramic bodies were treated with aqueous mixtures were prepared consisting of molybdenum salt and water, and prepared according to the method provided herein for Flexural Strength Test—3-Point Bend Strength. The ceramic bodies were treated by dipping the ceramic bodies in mixtures of 0.025 wt % and 0.5 wt % molybdenum (V) chloride (MoCl5) in water to infiltrate the thickness of the body, and tested for 3-point bend strength, according to the method described herein. Treated samples were dried and sintered at 1530° C. for 2.5 hours. The data for 11 repetitions were averaged, and the results are reported in Table 1.

TABLE 1

3-Point Bend Strength of Sintered Zirconia Bodies Treated with Antimicrobial Compositions.

|  | Untreated 3Y-TZP white bodies (Control) | Ex. 4 (0.025 wt % MoCl$_5$) | Ex. 5 (0.5 wt % MoCl$_5$) |
|---|---|---|---|
| Average (MPa) | 1064 | 1020 | 970 |
| Std dev (MPa) | 59 | 98 | 116 |
| Min(MPa) | 946 | 791 | 806 |
| Max(MPa) | 1172 | 1142 | 1122 |

Examples 6-10

Bisque stage zirconia bodies were treated with antimicrobial composition, sintered and tested for mechanical strength properties.

The effect of the antimicrobial compositions on the mechanical strength of sintered bodies was tested. Bisque stage shaded 3 mol % yttria-stabilized zirconia ceramic bodies (Shade 100, Glidewell Laboratories) were prepared according to the method provided herein for Biaxial Strength, and treated by dipping the ceramic bodies in aqueous mixtures consisting of 0.1 wt %, 0.3 wt %, 0.5 wt %. 1.0 wt % or 2.0 wt % molybdenum (V) chloride (MoCl$_5$) in distilled water to infiltrate the thickness of the body. The samples were dried and sintered at 1530° C. for 2 hours before testing for biaxial strength, according to the method described herein. The data for 11 repetitions were averaged, and the results are reported in Table 2.

TABLE 2

Biaxial Strength of Sintered Zirconia Bodies Treated with Antimicrobial Compositions.

|  | Control: Shade 100, 3Y-TZP | Ex. 6 0.1 wt % MoCl$_5$ | Ex. 7 0.3 wt % MoCl$_5$ | Ex. 8 0.5 wt % MoCl$_5$ | Ex. 9 1.0 wt % MoCl$_5$ | Ex. 10 2.0 wt % MoCl$_5$ |
|---|---|---|---|---|---|---|
| Average (MPa) | 1429 | 1278 | 1180 | 1152 | 1210 | 1067 |
| Std dev (MPa) | 136 | 73 | 143 | 171 | 122 | 33 |
| Min (MPa) | 1276 | 729 | 977 | 916 | 1006 | 1009 |
| Max (MPa) | 1559 | 1351 | 1325 | 1351 | 1241 | 1139 |

Examples 11 and 12

The chemical solubility of zirconia ceramic bodies treated with an aqueous molybdenum chloride antimicrobial mixture was tested.

Porous, white bisque stage BRUXZIR® HT 2.0 zirconia bodies were prepared by sanding the surface with #220 SiC sand paper, and were treated with one of two antimicrobial compositions consisting of either 0.3 wt % molybdenum (V) chloride (MoCl$_5$) or 0.5 wt % molybdenum (V) chloride (MoCl$_5$) in distilled water, to form the samples of Example 11 and Example 12, respectively. After dipping in the antimicrobial compositions for 10-30 seconds, the ceramic bodies were sintered at 1530° C. for 2 hours.

The samples were washed with water of grade 3 in accordance with ISO 3696. The specimens were dried at 150±5° C. for 4 hours, then weighed to the nearest 0.1 mg. The surface area was determined to the nearest 0.5 cm$^2$. Two 100 mL Pyrex glass bottles were prepared with 100 mL of 4% (by volume) acetic acid (analytical grade) solution in water of grade 3 as specified in ISO 3696 and preheated to 80±3° C. The specimens were placed into the preheated bottles. The bottles were closed and placed in an oven at 80±3° C. for 16 hours. The specimen was washed with water of grade 3 in accordance to ISO 3696 and dried at 150±5° C. to constant mass. The mass loss, in micrograms per square centimeter (µg/cm$^2$), was calculated for each sample and determined to be less than 1 µg/cm$^2$, meeting the limits for ISO68872:2008(E) Dentistry of 100 µg/cm$^2$ for chemical solubility.

Example 13

The amount of Mo metal ion present in a bisque ceramic dental restoration form treated with an antimicrobial composition was determined, as follows. A dental restoration in the shape of a molar was milled from a 3_mol % yttria stabilized zirconia bisque block by CAD/CAM technique, and weighed. The ceramic body was infiltrated with a 0.5_wt % MoCl$_5$ in distilled water by dipping the dental shape in a container containing the antimicrobial composition for 10-20 seconds under ultrasonic conditions. The dental shape was removed from the composition and dried under UV lamp dryer for 1 hour. After drying, the sample was re-weighed, and the amount of Mo metal in the dental shape was calculated to be 0.083 mol % of the dried bisqued, zirconia ceramic body.

Examples 14 and 15

Bisque stage zirconia bodies were treated with an antimicrobial molybdenum-containing composition comprising molybdenum in a light curing resin, sintered and tested for effectiveness against the growth of S. mutans.

Bisque stage 3 mol % yttria-stabilized zirconia ceramic bodies were prepared by sanding with #220 SiC sand paper. Antimicrobial compositions were prepared consisting of 0.3 wt % or 0.5 wt % molybdenum (V) chloride (MoCl$_5$) powder mixed in a light/heat curing dimethacrylate resin system suitable for use in dental applications. The ceramic bodies were painted with the molybdenum salt and resin mixture that infiltrated the porous bisque bodies, and then light cured, and sintered at 1530° C. for 2.5 hours.

The effectiveness of the samples in reducing growth of S. mutans was measured by calculating the percent reduction in bacterial growth compared to a control sample. A control sample comprising a 3 mol % yttria-stabilized zirconia ceramic not dipped in the molybdenum salt and resin composition, was tested for effectiveness in reducing bacterial growth of S. mutans (ATCC® 25175™). The control and samples were tested according to the method described in ASTM E2180-07 (2012). The results, showing percent reduction in bacterial growth are reported in Table 3.

TABLE 3

Reduction Of Bacterial Growth On Zirconia Ceramic Samples Treated with Molybdenum Salt In Resin-Based System And Strength.

| | Example No. | | |
|---|---|---|---|
| | Control (3Y zirconia) | Ex. 14 | 15 |
| Molybdenum salt concentration in resin | Control | 0.3 wt % | 0.5 wt % |
| Percent reduction S. mutans compared to control | — | 97.7% | 96.9% |
| 3 point Bend (MPa) | 1033 ± (44) | 1024 ± (64) | 987 ± (56) |

Examples 16- 18

A molybdenum-containing porcelain material was prepared that inhibited biofilm growth compared to a control.

Three pink shade porcelain wafers were prepared by mixing dental porcelain powder with three liquid molybdenum-containing compositions that comprised aqueous solutions of 0.1 wt %, 1.0 wt % and 5 wt %, molybdenum (V) chloride (MoCl5). Glass-ceramic (porcelain) material (GC Initial powder; 50:50 ratio of GU and TM, EO or EOP) was mixed with each of the three liquid molybdenum-containing compositions in about a 30:70 vol % molybdenum-containing liquid: porcelain powder to form three molybdenum-containing pastes. A control paste was prepared by mixing the porcelain powder with distilled water. Porcelain wafers having a thickness of about 2 mm were prepared from each the porcelain/molybdenum mixtures, and the control.

Biofilm testing of S. mutans was performed on the wafers according to the methods as follows, the results of which are reported in Table 4.

Biofilm testing was performed for S. mutans ATCC #25175 for a contact time of 48 hours (+2h), and contact temperature: 37 (+/−2° C.) (Sharukh S. Khajotia1, Kristin H. Smart1, Mpala Pilula1,3, David M. Thompson2: "Concurrent Quantification of Cellular and Extracellular Components of Biofilms" URL: http://www.jove.com/video/50639). Media and reagents used were as follows: tryptic soy broth, tryptic soy agar, D/E neutralizing broth, sterile 0.85% saline, biofilm growth medium (0.5X TY supplemented with 10 mM sucrose; 1.5% tryptone, 0.5% yeast extract, and 10 mM sucrose in sterile deionized water, and PBS.

A single colony of S. mutans was inoculated into 4 ml overnight TSA broth and incubated overnight at 37° C. for 16-18 hr. A 0.5 McFarland (105) unit dilution was made using the overnight culture in 10 ml of biofilm growth medium. Sterile specimens were transferred to sterile 12-well plates. 3 ml of diluted culture medium (0.5 McFarland unit) was added to wells with specimens and control, and then 3 ml of sterile uninoculated biofilm growth medium was added to sterility control wells.

The biofilms were grown under microaerophilic conditions, placing plates on a shaker (Heathrow Scientific hs120460 Digital Orbital Shaker) at 100 rpm inside an incubator at 37° C. After 24 hours the media was aseptically aspirated from all wells and washed twice with sterile PBS aspirating the PBS after each wash. Each well was replenished with 2 ml of fresh biofilm growth medium, and incubated for an additional 24 hours under identical conditions as the previous step, for total biofilm growth time of 48 hours. After 24 hours, biofilm were washed 3× with PBS buffer to remove planktonic microbes. Biofilms were aseptically removed from the specimen to 120 ml containing a sufficient volume of neutralizing broth to form an initial 1:10 dilution. Serial dilutions were made, plated and incubated for 48 hours (at 35-37° C.).

Bacterial colonies from each dilution series were counted and recorded. The percent reduction of bacteria from treated versus untreated samples was calculated. The results of the percent reduction in *S. mutans* is presented in Table 4.

TABLE 4

Results of Biofilm Testing On Molybdenum-Containing Porcelain Bodies.

| | Example # | | |
|---|---|---|---|
| | Ex. 16 (0.1 wt % $MoCl_5$) | Ex. 17 (1 wt % $MoCl_5$) | Ex. 18 (5 wt % $MoCl_5$) |
| Percent reduction | 99.85% | 99.93% | 99.98% |

The reduction of *S. mutans* for sample porcelain bodies comprising a molybdenum-containing component was greater than 99.8% compared to the control, for all sample materials.

Examples 19-21

Sintered zirconia ceramic bodies (3 mol % yttria stabilized zirconia), prepared by coating sintered bodies with a molybdenum-containing composition, inhibited biofilm growth for *S. mutans* compared to a control.

Porous, white bisque stage BRUXZIR® HT 2.0 zirconia wafers (28 mm×28 mm×1 mm) were prepared by sanding the surface with #220 SiC sand paper. Three liquid molybdenum-containing compositions were prepared that comprised aqueous solutions of 0.1 wt %, 1.0 wt % and 5 wt %, of molybdenum (V) chloride ($MoCl_5$) in distilled water to infiltrate the thickness of the ceramic bodies. The samples were dried and sintered at 1530° C. for 2 hours. Biofilm testing was performed for *S. mutans* ATCC #25175, on samples that were incubated for 48 hours, substantially according to Examples 16-18. The results are reported in Table 5. After 48 hours the control had 5.75E+09 colony forming units (CFU).

TABLE 5

Results of Biofilm Testing On Sintered Molybdenum-Containing Zirconia Bodies.

| | Example No. | | |
|---|---|---|---|
| | Ex. 19 (0.1 wt % $MoCl_5$) | Ex. 20 (0.1 wt % $MoCl_5$) | Ex. 21 (0.1 wt % $MoCl_5$) |
| CFU | 8.45E+05 | 4.00E+05 | 1.00E+05 |
| Percent reduction | 99.99% | 99.99% | 100% |

After an incubation period of 48 hours, the percent reduction in biofilm growth was over 99% for all samples.

Example 22

Sintered zirconia ceramic bodies (3 mol % yttria stabilized zirconia) were prepared by coating sintered bodies with a molybdenum-containing composition that showed an inhibitory effect on biofilm growth for *P. gingivalis* compared to a control.

Porous, white bisque stage BRUXZIR® HT 2.0 zirconia wafers (28 mm×28 mm×1 mm) were prepared by sanding the surface with #220 SiC sand paper. A liquid molybdenum-containing composition was prepared that comprised aqueous solutions of 0.1 wt % of molybdenum (V) chloride ($MoCl5$) in distilled water to infiltrate the thickness of the porous ceramic bodies. The samples were dried and sintered at 1530° C. for 2 hours.

The effectiveness of the samples in reducing growth of *P. gingivalis* was measured by calculating the percent reduction in bacterial growth compared to a control sample comprising a 3 mol % yttria-stabilized zirconia ceramic that was not dipped in the aqueous molybdenum solution. The control and samples were tested according to the method described in ASTM E2180-07 (2012). The percent reduction of *P. gingivalis* was over 87% (87.4%) for ceramic bodies infiltrated with an aqueous solution of 0.1 wt % molybdenum, compared to the control.

I claim:

1. A method of making a sintered ceramic dental prosthesis for restoring dentition of a patient that inhibits bacterial growth, comprising
   a. obtaining a porous ceramic body comprising a shape of a dental prosthesis,
   b. obtaining a liquid molybdenum-containing composition comprising from 0.015 wt % to 5 wt % of a molybdenum-containing component, based on the weight of the molybdenum-containing composition,
   c. infiltrating the liquid molybdenum-containing composition into a first portion of the porous ceramic body that corresponds to a portion of the sintered ceramic body that contacts a gingival surface of the patient, and
   d. sintering the infiltrated porous zirconia ceramic to form the sintered ceramic dental prosthesis.

2. The method of claim 1, wherein the liquid molybdenum-containing composition is an aqueous solution.

3. The method of claim 1, wherein the liquid molybdenum-containing composition comprises a resin.

4. The method of claim 1, wherein the molybdenum-containing component comprises a molybdenum-containing salt.

5. The method of claim 1, wherein the molybdenum-containing component comprises molybdenum (V) chloride ($MoCl_5$).

6. The method of claim 1, wherein the liquid molybdenum-containing composition comprises from 0.015 wt % to 3 wt % of the molybdenum-containing component, based on the weight of the molybdenum-containing composition.

7. The method of claim 1, wherein the liquid molybdenum-containing composition comprising 0.015 wt % to less than 0.1 wt % of the molybdenum-containing component, based on the weight of the molybdenum-containing composition.

8. The method of claim 1, wherein the dental prosthesis is an implant, and the porous zirconia ceramic body is fully infiltrated with the liquid molybdenum-containing composition.

9. The method of claim 1, wherein the dental prosthesis is a crown, and the first portion corresponds to an intaglio surface or a margin of the sintered ceramic dental prosthesis.

10. The method of claim 1, wherein the dental prosthesis is a crown, and the first portion corresponds to a cervical third region of the sintered ceramic dental prosthesis.

11. The method of claim 1, wherein the dental prosthesis is an implant abutment and the first portion corresponds to a subgingival portion when the sintered ceramic dental restoration is installed in the mouth of a user.

12. The method of claim 1, wherein the porous ceramic body comprises an yttria-stabilized zirconia.

13. The method of claim 1, wherein the sintering step is performed at a sintering temperature greater than 800° C.

14. The method of claim 1, wherein the porous body comprises a second portion that is not infiltrated with the liquid molybdenum-containing composition, and the second portion corresponds to a vestibular surface of an incisal region of the sintered dental restoration.

* * * * *